(12) United States Patent
Winn

(10) Patent No.: US 8,435,217 B2
(45) Date of Patent: May 7, 2013

(54) GAS STERILIZABLE TWO-PART POLYMER DELIVERY SYSTEM

(75) Inventor: R. Alastair Winn, Santa Barbara, CA (US)

(73) Assignee: Applied Silicone Corporation, Santa Barbara, CA (US)

( * ) Notice: Subject to any disclaimer, the term of this patent is extended or adjusted under 35 U.S.C. 154(b) by 138 days.

(21) Appl. No.: 12/101,926

(22) Filed: Apr. 11, 2008

(65) Prior Publication Data

US 2009/0259170 A1  Oct. 15, 2009

(51) Int. Cl.
*A61M 5/32* (2006.01)

(52) U.S. Cl.
USPC .............................. 604/199; 604/82

(58) Field of Classification Search .............. 604/82, 604/191, 199, 222
See application file for complete search history.

(56) References Cited

U.S. PATENT DOCUMENTS

| | | | |
|---|---|---|---|
| 2,860,635 A | 11/1958 | Wilburn | |
| 3,930,499 A | 1/1976 | Rimbaud | |
| 3,937,219 A * | 2/1976 | Karakashian | 604/26 |
| 4,340,067 A | 7/1982 | Rattenborg | |
| 5,620,425 A | 4/1997 | Heffernan et al. | |
| 5,986,002 A | 11/1999 | Hwang et al. | |
| 6,189,195 B1 | 2/2001 | Reilly et al. | |
| 6,234,994 B1 * | 5/2001 | Zinger | 604/82 |
| 6,471,671 B1 * | 10/2002 | Urick et al. | 604/98.01 |
| 6,530,896 B1 | 3/2003 | Elliot | |
| 6,610,033 B1 | 8/2003 | Melanson et al. | |
| 2001/0039402 A1 | 11/2001 | Prais et al. | |
| 2003/0199824 A1 * | 10/2003 | Mahoney et al. | 604/155 |
| 2005/0008528 A1 | 1/2005 | Prabhu et al. | |
| 2005/0101920 A1 * | 5/2005 | Keane et al. | 604/218 |
| 2005/0113763 A1 | 5/2005 | Reynolds | |
| 2006/0027467 A1 * | 2/2006 | Ferguson | 206/63.3 |
| 2006/0069356 A1 | 3/2006 | Witowski | |
| 2006/0178747 A1 | 8/2006 | de Vries et al. | |
| 2006/0192165 A1 | 8/2006 | Matkovich et al. | |
| 2006/0206209 A1 * | 9/2006 | Cragg et al. | 623/17.16 |
| 2006/0274601 A1 | 12/2006 | Seaton, Jr. | |
| 2007/0010824 A1 | 1/2007 | Malandain et al. | |
| 2007/0021835 A1 | 1/2007 | Edidin | |
| 2007/0179620 A1 | 8/2007 | Seaton, Jr. | |
| 2008/0152536 A1 | 6/2008 | Fischer et al. | |

FOREIGN PATENT DOCUMENTS

| | | |
|---|---|---|
| DE | 102007015010 A1 | 10/2008 |
| EP | 0882436 A1 | 12/1998 |

OTHER PUBLICATIONS

Zhang, H.; et.al. "The permeability characteristics of silicone rubber" (2006) by SAMPE.*
Zhang, H.; et.al. "The permeability characterisitcs of silicone rubber" (2006) by SAMPE.*
Extended European Search Report dated Sep. 7, 2012 in the corresponding European Patent Application No. 09730779.7.

* cited by examiner

*Primary Examiner* — Tatyana Zalukaeva
*Assistant Examiner* — Brandy C Scott
(74) *Attorney, Agent, or Firm* — John K. Fitzgerald; Fulwider Patton LLP

(57) ABSTRACT

A gas sterilizable delivery system for a two-part polymer system is provided. The delivery system includes at least two syringe barrels, each barrel being sealed with a gas permeable plunger seal allowing permeation of a sterilant gas to permeate through the plunger seal allowing the entire assembly to be gas sterilized.

20 Claims, 1 Drawing Sheet

GAS STERILIZABLE TWO-PART POLYMER DELIVERY SYSTEM

BACKGROUND

This invention relates to a system or apparatus for mixing and delivering a two-part polymer material to various locations of a human body. In particular, the present invention provides a system that allows for ethylene-oxide sterilization of pre-packaged polymer components that are mixed when extruded from a syringe delivery system.

In many orthopedic or reconstructive surgical procedures it is common to use polymer based adhesives, cements or spatial fill materials to either attach implants or artificial joints to bones or joint structures or to fill cavities in a persons soft tissue or soft tissue supporting structures to achieve a desired reconstructive result. These adhesives or fill materials are typically formed in place by co-extruding a base material and a second material that may contain appropriate catalysts and the like, intermixing the materials so that when they are extruded into position they begin to cure into the final, hardened material.

In some prior art systems, the material are mixed in a separate mixing vessel and then loaded into an extrusion device. This process is disadvantageous because such mixing and loading typically exposes an operator to an offensive odor, is time consuming and may be messy. Additionally, the component materials may be difficult to handle.

Another problem with such a prior art system is that the mixing processing results in air being included into the adhesive. Since such entrapped air may reduce the performance of the adhesive or filling material, it must be removed prior to use. Typically air is removed from the mixture by applying a vacuum to the mixture, or by mixing the two components of the final material under a vacuum. This requires additional equipment, which may preclude mixture of the components in a location convenient to use of the material.

One solution to these problems has been to develop a double barrel syringe system with each component pre-packaged in its individual barrel. When the plunger of the system is activated, both of the materials are co-extruded through a mixing nozzle, the specifications of which may be precisely engineered to deliver a properly mixed material at the use end of the nozzle. In this way the two components may be packaged in a single unit, de-aired, and be ready for use. Another advantage of such a system is that final material may be prepared in a desired amount. If more material is needed, a second, third and so forth syringe assembly may be used.

While such two barreled systems have been shown to be quite useful in many applications, sterilization of the component materials of such system has been problematic because the components may be damaged by the method used to sterilize the system. For example, while dry heat may be acceptable, high temperatures and long sterilization cycles can damage not only the polymer components, but also the delivery system and its packaging. Steam sterilization is also unsuitable because steam does not easily pass in and out of a closed system and the packaging and delivery system may not be capable of withstanding the high temperatures without chemical and/or physical damage.

High energy radiation, such as gamma radiation or e-beam sterilization are not suitable because the energy of these methods imparted into the polymer components may cause crosslinking or gelling of the component materials during the sterilization process are typically heat sensitive and thus can be degraded if heat sterilized. Additionally, gas sterilization, such as with ethylene oxide, has been problematic because the materials used to form the barrel and plungers of the syringe system have not been sufficiently permeable to the gas to allow transmission of the gas into the components to adequately sterilize them. Sterilization of components by filtering the components prior to adding the components to the syringe barrel has been found to provide a sterile product, but is expensive and requires special clean-rooms and expensive control methods to ensure sterility.

What has been needed, and heretofore unavailable, is an inexpensive syringe system designed from mixing and delivery of two part polymer systems that may also be gas sterilized, thus eliminating the need for pre-sterilization or aseptic packing, or a second sterilization step after the syringe is placed in its final packaging. Such a system would also be advantageous in that a filled two-part syringe assembly could be simply placed into a bag, tray, box or kit and sealed into a gas permeable pouch made from a material such as Tyvek and sterilized. The present invention fills these, and other needs.

SUMMARY OF THE INVENTION

In one aspect, the present invention includes a system for mixing and dispensing a two-component polymer system, comprising a first elongated cylindrically shaped member having a lumen extending therethrough for storing a first component, the first elongated cylindrically shaped member also having an opening disposed at one end and an exit port disposed at another end; a second elongated cylindrically shaped for storing a second component such that the first and second components are isolated from each other, the second elongated cylindrically shaped member also having an opening disposed at one end and an exit port disposed at another end; a first plunger having a pusher end and a first gas permeable seal disposed at a seal end of the first plunger, the first plunger and first gas permeable seal configured to be received in the opening of the first elongated cylindrically shaped member to seal the first component in the lumen of the elongated cylindrically shaped member and to provide pressure on the first component stored in the lumen of the first elongated cylindrically shaped member when a force is applied to the pusher end of the first plunger to extrude the first component from the lumen of the first elongated cylindrically shaped member through the exit port of the first elongated cylindrically shaped member; a second plunger having a pusher end and a second gas permeable seal disposed at a seal end of the second plunger, the second plunger and second gas permeable seal configured to be received in the opening of the second elongated cylindrically shaped member to seal the second component in the lumen of the second elongated cylindrically shaped member and to provide pressure on the second component stored in the lumen of the second elongated cylindrically shaped member when a force is applied to the pusher end of the second plunger to extrude the second component from the lumen of the second elongated cylindrically shaped member through the exit port of the second elongated cylindrically shaped member; and a mixing nozzle in communication with the exit ports of the first and second elongated cylindrically shaped members for receiving and mixing the first and second components as they are extruded from the first and second barrels.

In an additional aspect, the first and second gas permeable seals are capable of being sterilized using ethylene oxide. In still another aspect, the first component is an uncured silicone, and in yet another aspect, the first component is a liquid silicone and the second component contains a catalyst for curing the first and second components. In yet another aspect, at least one of the first and second elongated cylindrically shaped members are formed of a gas permeable material.

In a further aspect of the present invention, the system may be used for surgical repair of bone; in another aspect, the system may be used for surgical repair of vascular damage, and particularly where the vascular damage repaired is an aneurysm. In accordance with a still further aspect of the present invention, the system may be used for surgical repair of tissue or bone in direct contact with brain tissue. In yet a further aspect, the system may be used during reconstructive surgery to fill voids or adhere tissue where necessary.

Still another aspect of the present invention includes sterilizing the system described above using a gas sterilant. In one additional aspect, the gas sterilant is ethylene oxide.

In yet another aspect, the present invention includes a method of providing a sterilized two-part polymer system for use during surgery, comprising providing a delivery system having two syringe barrels, each syringe barrel configured to receive one component of a two-part polymer system; filing one of the two syringe barrels with a first component of a two-part polymer system and filling the other of the two syringe barrels with a second component of the two-part polymer system; inserting a gas permeable plunger within each syringe barrel to maintain the component of the two-part polymer system filling the syringe barrel in the syringe barrel; and sterilizing the filled delivery system using a gas sterilant. In an additional aspect, the gas sterilant is ethylene oxide.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

The present invention provides a delivery system for a polymer system comprising two components, wherein the components when mixed cure into a material useful for adhering implants to body tissue or adhering body tissue to other body tissue, such as bone. Additionally, the cured material may have other uses, such as may be required during cosmetic or reconstructive surgery.

Figure 1:
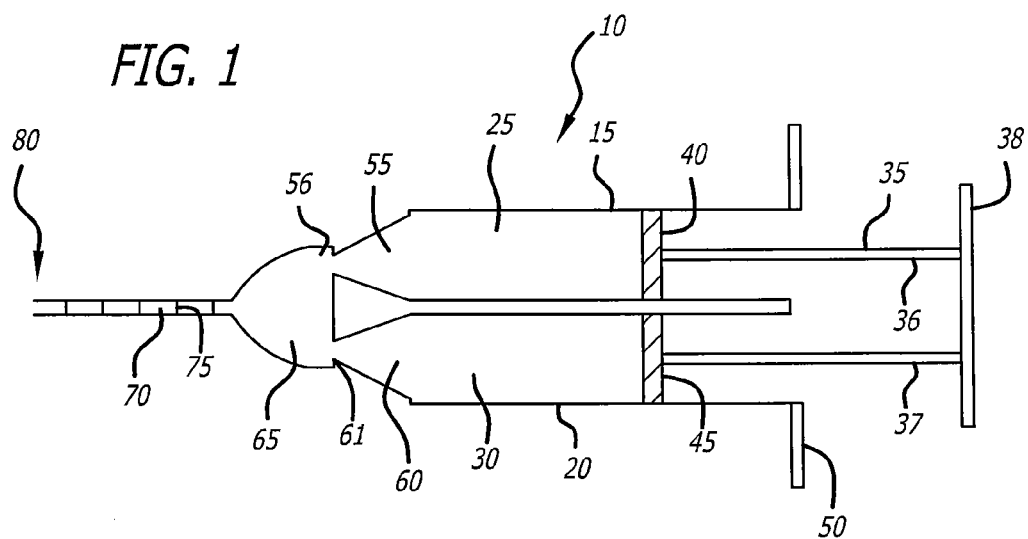
FIG. 1 is a cross-sectional view of a two-component syringe system is accordance with an embodiment of the present invention.

FIG. 1 illustrates one embodiment of the present invention showing a double syringe system that may be preloaded with the components of a two-component polymer system and then sterilized utilizing gas sterilization, such as, for example, sterilization using ethylene oxide, a process well known in the art. Unlike prior two component delivery systems, which could not be sterilized using gas sterilization because the components of the delivery system were not permeable to the sterilant, the delivery system of the present invention includes features which provide from permeability to the sterilant. This is advantageous as previous systems could only be sterilized using heat sterilization, which limited the polymer components that could be used, as such components are typically sensitive to heat, and would be degraded by the sterilization process.

As shown in FIG. 1, a two-component delivery system 10 in accordance with the present invention includes a first syringe barrel 15 that can be preloaded with a first component 25 of a polymer system and a second syringe barrel 20 that can be preloaded with a second component 30 of a polymer system. A plunger 35 is used to force the components 25 and 30 from the first and second syringes 15, 20.

As shown in FIG. 1, plunger 35 has a first plunger shaft 36 disposed at a distal end of the shaft 36 for pushing a plunger seal 40 into the first syringe barrel 15 to extrude first component 25 from the first barrel. Plunger 35 also has a second plunger shaft 37 for pushing a plunger seal 45 disposed at a distal end of shaft 37 into the second syringe barrel 20 to extrude second component 30 from the second barrel. First and second pusher shafts 36, 37 are joined at their respective proximal ends to a pushing means 38. Pushing means 38 cooperates with lip 50 disposed at a proximal end of barrels 15 and 20 to allow the delivery system 10 to be held in one hand, and using one hand, to provide from pressure to be applied to plunger seals 40 and 45 through plunger shafts 36 and 37 to extrude the first and second components 25 and 30 of the polymer system from the first and second syringe barrels 15, 20 simultaneously.

The first syringe barrel 15 has a tapered portion 55 that tapers to an outlet port 56. Similarly, the second syringe barrel 20 has a tapered portion 60 that tapers to an outlet port 61. Tapered portion 55, and 60 typically with have an extended neck that may either be sized to be received by a mixing nozzle 65, or may terminate in a connector, such as a Luer connecter, known in the art.

In the embodiment shown in FIG. 1, mixing nozzle 65 is configured to receive the tapered portions 55 and 60 of first and second syringe barrels 15 and 20. In this embodiment, first component 25 extrudes through outlet port 56 into mixing nozzle 65 and second component 30 extrudes through outlet port 61 in mixing nozzle 65.

Continued pressure upon pushing means 38 causes the first and second components 25 and 30 of the polymer system to be forced through the mixing nozzle. In the embodiment shown, the first and second components of the polymer system are forced into the mixing nozzle which has a mixing portion 70. As the first and second components of the polymer system are forced through the mixing portion 70, convolutions or other means causes the components to be thoroughly mixed together before they are extruded through outlet port 80 of the mixing nozzle 65.

While the embodiment of the mixing nozzle illustrated in FIG. 1 is shown having a receiving portion for receiving the first and second components of the polymer system and a separate mixing portion, those skilled in the art will appreciate that the mixing nozzle may have other configurations which accomplish the same function without departing from the scope of the present invention. For example, the mixing nozzle may be configured such that mixing begins immediately when the first and second components of the polymer system enter the mixing nozzle.

Figure 2:
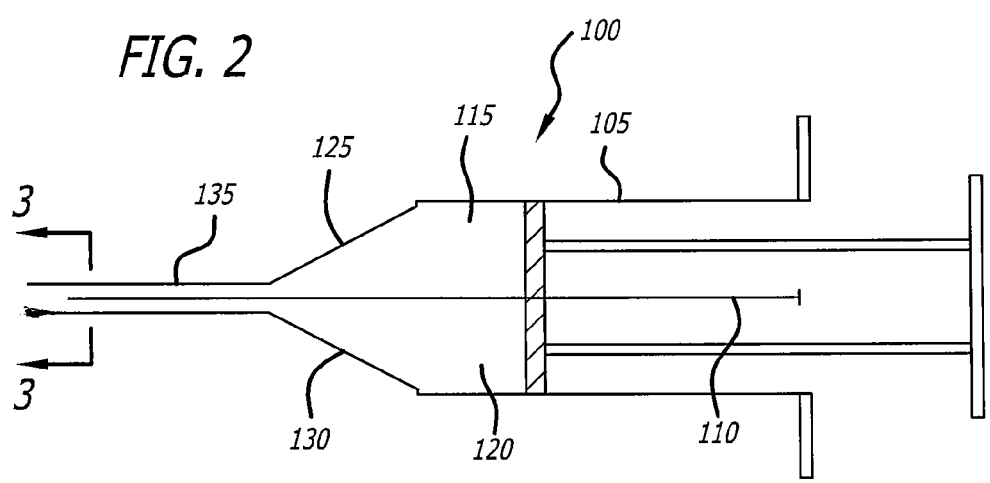
FIG. 2 is a cross-section view of another embodiment of a two-component syringe system in accordance with the present invention.

FIG. 2 illustrates another exemplary embodiment of the delivery system in accordance with the present invention. In this embodiment, the double syringe system comprises a cylindrical outer wall 105. An inner wall 110 is disposed within cylindrical outer wall 105, forming chambers 1115 and 120, which in turn will hold the first and second components of the polymer system to be delivered. Inner wall 110 extends completely through tapered portions 125 and 130 of chambers 115 and 120, and through a nozzle portion 135.

Figure 3:
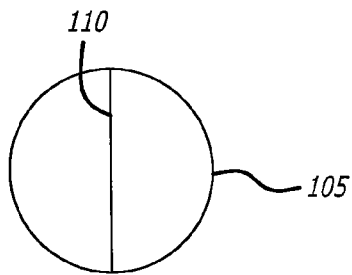
FIG. 3 is perspective view sighting along a flow axis of a nozzle of the embodiment of FIG. 2 showing the arrangement of the inner and outer walls of the nozzle.

Further detail of nozzle portion 135 is shown in FIG. 3, where inner wall is shown to bisect the annular space created within cylindrical outer wall 105. The diameter of the nozzle portion 135 may be sized and configured, such as by tapering, to be received in a connect, such as, for example, a Luer connector, for connection to a mixing nozzle.

In still another embodiment, the nozzle portion 135 may be configured as a mixing nozzle by altering the configuration of the inner wall 110 and providing convolutions or other mixing means within a distal portion of nozzle portion 135 to ensure that the two components of the polymer system are completely mixed as they are extruded through the nozzle portion. Additionally, the length of the nozzle portion may be extended sufficiently to allow for delivery of the mixed polymer system a desired location. This embodiment is advantageous in that the entire system is of unitary constructions, thus eliminating the requirement for a mixing nozzle.

Plunger seals 40 and 45 (FIG. 1) may be made from a variety of materials having a gas permeability to air in the range of $500\text{-}30{,}000 \times 10^{-9}$ cm$^2$/sec/atm at 80° C., and preferably greater than $10{,}000 \times 10^{-9}$ cm$^2$/sec/atm. Further, the materials forming the plunger seal must not be damaged by absorption of the components of the polymer system being delivered by the delivery system of the present invention, nor should the plunger seals swell when in contact with the contents of the syringe barrels. Moreover, the plunger seals must be free of residual catalysts or extractable components that could leach from the plunger seals and contaminate the polymer components contained in the syringe barrels. Examples of materials that are suitable for this purpose are dimethyl, diphenyl, and methyl-trifluoropropyl copolymer silicone elastomers having durometers in the range of 20-80 Shore A, among other silicones.

In another embodiment, the plunger may be made of a gas permeable material, such as rubbers or polymers known in the art, and then may have a gas permeable material that is compatible with the contents of the syringe. The permeable portion of the plunger seal may be in the form of one molded piece or may be part of a multi-part structure including an embodiment with an o-ring or lip type seal against the inner wall of the syringe barrel. Materials such as, for example, Tyvek (E.I. DuPont de Nemours) and Gortex (W.L. Gore, Inc.) can be used.

In still another embodiment, the syringe barrel and/or proximal seals of the plunger may also be formed from materials that are permeable to gas sterilants. Any gas permeable material, such as, for example, silicone-polyethylene, silicone-acrylic or silicone-polyurethane copolymers, among others, that may be formed into a syringe barrel or body and plunger seals can be used provided that it is compatible with the components of the polymer system to be contained within the syringe barrel.

The contents of the two barrels of the delivery system of the present invention will typically be components, that when mixed, provide what is known in the art as a cure-in-place polymer. Any polymer system that can be divided in "A" and "B" components that are compatible with the gas permeable plunger seal material used to form the plunger seals may be used. Those skilled in the art will understand that "A" and "B" components are typically defined as being a first component that includes the at least one of polymers being polymerized to give the final cured material, and a second component that may include one or more additional monomers or polymers along with a catalyst and possible a cross-linking agent. In such systems, when components "A" and "B" are mixed, the catalyst initiates the polymerization reaction between the included monomers, polymers and cross-linking agent resulting in the final cured (that is, polymerized) material. Such reactions typically are complete at room temperature within two hours, and preferably within twenty minutes.

The uncured components typically range in viscosity from 100 to 500,000 centipoise, and preferably from 2,000 to 50,000 centipoise. Components have such viscosities can be extruded from the delivery system in accordance with the present invention using hand generated force. Higher viscosity components can also be extruded using any kind of air driven or mechanical apparatus designed for the purpose.

Suitable silicone uncured elastomer system that have been approved for long term implantation in accordance with the requirements of ISO 10993 are platinum catalyzed two part vinylpolysiloxane silicone products such as, for example, those formulated by Applied Silicone Corporation of Santa Paula, Calif. This material can be provided in a variety of kits that form elastomers ranging from 5 to 70 Shore A durometer. Another suitable silicone elastomer is a tin catalyzed two part system such as Dow Corning Medical Grade 382, formulated by Dow Corning Corporation. Two part curing materials other than silicones, such as urethanes, epoxies and acrylics, may also be suitable for gas sterilization in a system utilizing gas permeable syringes, proximal seals or plunger seals in accordance with the present invention.

While several particular forms of the invention have been illustrated and described, it will be apparent that various modifications can be made without departing from the spirit and scope of the invention.

I claim:

1. A single use gas sterilizable syringe system configured for mixing and dispensing a pre-loaded two-component polymer system, comprising:

a first elongated cylindrically shaped member having a lumen extending therethrough for storing a first polymer component, the first elongated cylindrically shaped member also having an opening disposed at one end and an exit port disposed at another end, the first polymer component being sterilized by a gas sterilant while stored in the lumen of the first elongated cylindrically shaped member;

a second elongated cylindrically shaped member for storing a second component such that the first and second components are isolated from each other, the second elongated cylindrically shaped member also having an opening disposed at one end and an exit port disposed at another end;

a first plunger having a pusher end and a first seal disposed at a seal end of the first plunger, the first plunger and first seal configured to be received in the opening of the first elongated cylindrically shaped member to seal the first polymer component in the lumen of the elongated cylindrically shaped member and to provide pressure on the first polymer component stored in the lumen of the first elongated cylindrically shaped member when a force is applied to the pusher end of the first plunger to extrude the first polymer component from the lumen of the first elongated cylindrically shaped member through the exit port of the first elongated cylindrically shaped member, the first seal having a gas permeability of at least $500 \times 10^{-9}$ cm$^2$/sec/atm at 80° C. and is permeable by a gas sterilant to allow for sterilization of the first polymer component stored in the lumen of the first elongated cylindrically shaped member, and the first seal made of a material compatible with the first polymer component and which does not absorb the first polymer component;

a second plunger having a pusher end and a second seal disposed at a seal end of the second plunger, the second plunger and second seal configured to be received in the opening of the second elongated cylindrically shaped member to seal the second component in the lumen of the second elongated cylindrically shaped member and to provide pressure on the second component stored in the lumen of the second elongated cylindrically shaped member when a force is applied to the pusher end of the second plunger to extrude the second component from the lumen of the second elongated cylindrically shaped member through the exit port of the second elongated cylindrically shaped member, the second seal having a gas permeability of at least $500 \times 10^{-9}$ cm$^2$/sec/atm at 80° C. and is permeable by a gas sterilant to allow for sterilization of the second component stored in the lumen of the second elongated cylindrically shaped member, and the second seal made of a material compatible with the second component and which does not absorb the second component; and a mixing nozzle in communication with the exit ports of the first and second elongated cylindrically shaped members for receiving and mixing the first polymer component and the second component as they are extruded from the first and second barrels.

2. The system of claim 1, wherein the gas sterilant is ethylene oxide.

3. The system of claim 1, wherein the first polymer component is an uncured silicone.

4. The system of claim 1, wherein the first polymer component is a liquid silicone and the second component contains a catalyst for curing the first and second components.

5. The system of claim 1, wherein the system is used for surgical repair of bone.

6. The system of claim 1, wherein the system is used for surgical repair of vascular damage.

7. The system of claim 6, wherein the vascular damage repaired is an aneurysm.

8. The system of claim 1, wherein the system is used for surgical repair of tissue or bone in direct contact with brain tissue.

9. The system of claim 1, wherein the system is used during reconstructive surgery.

10. The system of claim 1, wherein at least one of the first and second elongated cylindrically shaped members are formed of a gas permeable material that is permeable by a gas sterilant.

11. The system of claim 10, wherein the gas sterilant is ethylene oxide.

12. The system of claim 1, wherein the second component in the second elongated cylindrically shaped member includes a polymer.

13. A method of providing a sterilized single use syringe system having a two-part polymer system for use during surgery, comprising:

providing a syringe delivery system having two syringe barrels, each syringe barrel configured to receive one component of a two-part polymer system;

filing one of the two syringe barrels with a first component of a two-part polymer system and filling the other of the two syringe barrels with a second component of the two-part polymer system;

inserting a plunger within each syringe barrel to maintain the component of the two-part polymer system filling the syringe barrel in the syringe barrel, each plunger having a gas permeability of at least $500 \times 10^{-9}$ cm$^2$/sec/atm at 80° C. and is permeable by a gas sterilant to allow for sterilization of the components of the two-part polymer system in the syringe, and each plunger made of a material compatible with both the first and second components of the two-part polymer system and which does not absorb the components of the two-part polymer system, even during sterilization; and sterilizing the filled syringe delivery system using a gas sterilant.

14. The method of claim 13, wherein the gas sterilant is ethylene oxide.

15. The method of claim 13, wherein sterilizing the filled delivery system includes placing the delivery system in a gas permeable pouch, sealing the pouch and sterilizing the pouch.

16. The system of claim 1, wherein at least one of the first and second seals has a gas permeability of at least $10,000 \times 10^{-9}$ cm$^2$/sec/atm at 80° C.

17. The method of claim 13, wherein at least one of the first and second plungers has a gas permeability of 500 to $30,000 \times 10^{-9}$ cm$^2$/sec/atm at 80° C.

18. The method of claim 13, wherein at least one of the first and second plungers has a gas permeability of at least $10,000 \times 10^{-9}$ cm$^2$/sec/atm at 80° C.

19. The system of claim 1, wherein at least one of the first and second seals is formed from a fluoro-silicone.

20. The system of claim 13, wherein at least one of the first and second plungers is formed from a fluoro-silicone.

* * * * *